United States Patent [19]

Lamberti

[11] Patent Number: 5,827,707
[45] Date of Patent: Oct. 27, 1998

[54] METHOD FOR MANUFACTURING MINIMAL VOLUME CAPSULES CONTAINING BIOLOGICAL MATERIALS

[75] Inventor: Francis Lamberti, Irvine, Calif.

[73] Assignee: Neocrin Company, Irvine, Calif.

[21] Appl. No.: 484,778

[22] Filed: Jun. 7, 1995

[51] Int. Cl.[6] .............................. A61K 9/50; B01J 13/20; C12N 5/06
[52] U.S. Cl. ........................... 435/178; 264/4.1; 264/4.3; 424/424; 424/493; 435/382; 425/5; 514/866
[58] Field of Search .............................. 264/4.3; 424/424, 424/493; 435/240.22, 178; 514/866

[56] References Cited

U.S. PATENT DOCUMENTS

| | | | |
|---|---|---|---|
| 4,352,883 | 10/1982 | Lim | 435/178 |
| 4,689,293 | 8/1987 | Goosen et al. | 435/240.22 X |
| 4,798,786 | 1/1989 | Tice et al. | 435/240.22 X |
| 4,822,535 | 4/1989 | Ekman et al. | 264/4.3 |
| 4,927,761 | 5/1990 | Reading et al. | 435/240.22 X |
| 5,175,093 | 12/1992 | Seifert | 435/240.22 X |
| 5,529,914 | 6/1996 | Hubbell et al. | 424/493 X |

*Primary Examiner*—Richard D. Lovering
*Attorney, Agent, or Firm*—Lyon & Lyon LLP

[57] ABSTRACT

The present invention provides methods and a device for producing minimal volume capsules containing viable cells or cellular aggregates. The methods and device use a two-phase aqueous emulsion system to form a dispersion of liquid capsule-forming materials in a continuous liquid phase to which is added a suspension of biological material. Alternatively, the biological material can be added to one or the other of the liquid phases. The composition of this emulsion is adjusted to promote the thermodynamically-driven process of particle engulfment by the dispersed droplets of liquid capsule-forming materials. Subsequently, the droplets engulf the biological material to form a liquid film surrounding the tissue and are converted to solid form, resulting in encapsulation of the biological material in minimum volume capsules.

15 Claims, 6 Drawing Sheets

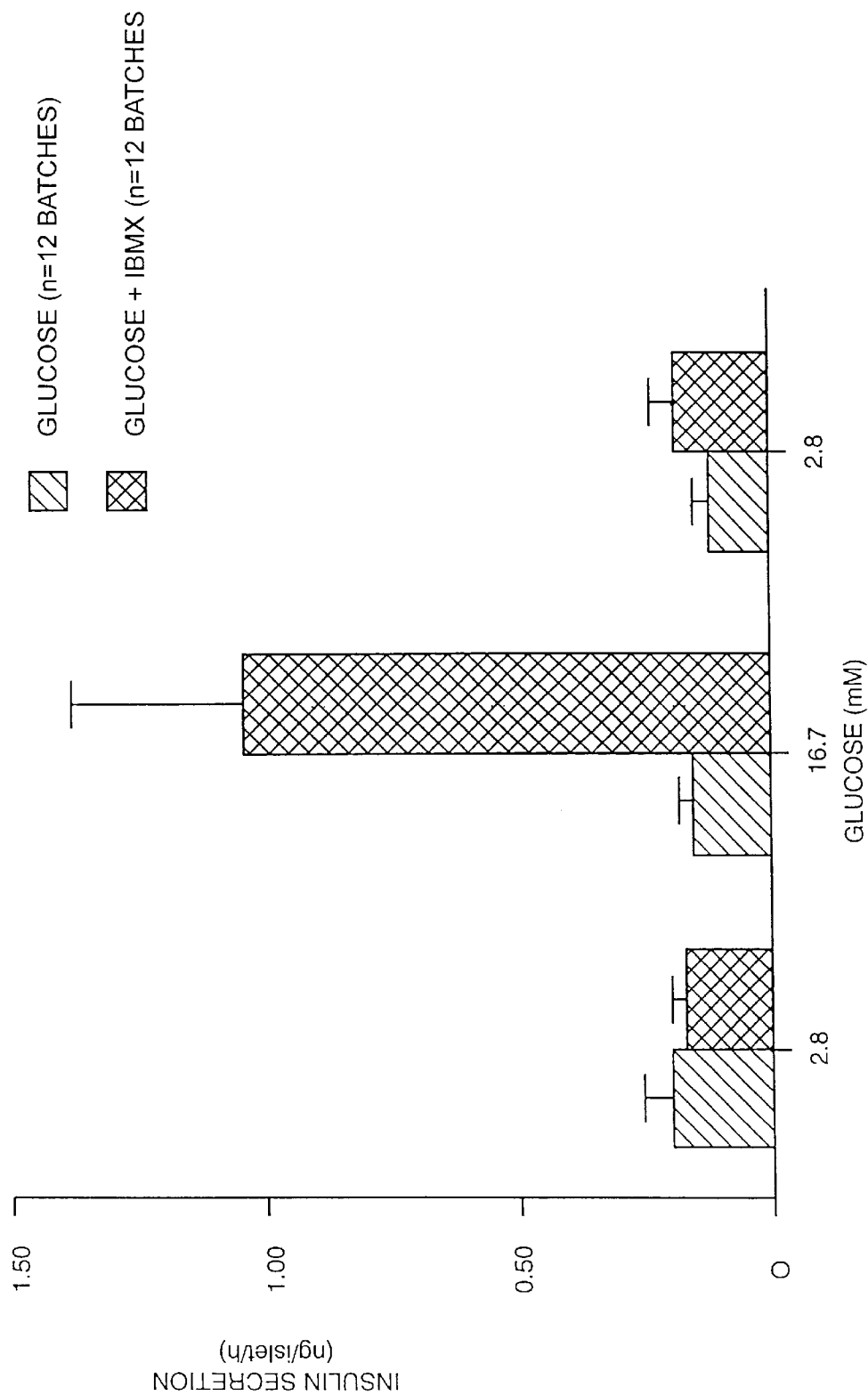

METHOD FOR MANUFACTURING MINIMAL VOLUME CAPSULES CONTAINING BIOLOGICAL MATERIALS

BACKGROUND

Microencapsulation of cells and/or cell aggregates for implantation in an animal is an area or research currently attracting much interest. The use of microcapsules provides the potential for such medically important procedures as treatment of insulin-dependent diabetes mellitus (IDDM) in humans through transplantation of insulin-producing cells or cell aggregates, and timed release or long term delivery of drugs to an animal.

A variety of procedures for encapsulating useful cells have previously been tried. These procedures include coating cells with both polyanionic and polycationic layers to create a membrane around the cells which is impermeable to antibodies and other elements of the immune response. See for example Lim U.S. Pat. No. 4,352,883, Lim U.S. Pat. No. 4,391,909, Lim U.S. Pat. No. 4,409,331, Tsang et al. U.S. Pat. No. 4,663,286, Goosen et al. U.S. Pat. No. 4,673,566, Goosen et al. U.S. Pat. No. 4,689,293, Rha et al. U.S. Pat. No. 4,744,933, Rha et al. U.S. Pat. No. 4,749,620, and Goosen et al. U.S. Pat. No. 4,806,355.

Biocompatibility problems have arisen with a number of these prior art methods. The body soon rejects the material, creating a coat of fibroblasts which impair transport of oxygen and other nutrients into the microcapsules and the desired cell products out of the microcapsules. Hubbell et al. U.S. Pat. No. 5,232,984, Hubbell et al. U.S. Pat. No. 5,380,536 and Hubbell U.S. Pat. No. 5,410,016 describe methods for increasing the biocompatibility of the encapsulation material.

These prior art capsules are formed either by (i) the formation of ionic cross-linking (e.g. alginate or carrageenan), (ii) a change in temperature (e.g. agarose or carrageenan), (iv) photopolymerization, or (iv) solvent precipitation (e.g. p(HEMA), Crooks, C. A., et al., J. Biomed. Mater. Res. 24:1241–1262 (1990)).

Other methods, such as the use of a surrounding device, have been employed in an attempt to permit integration of the implanted cells or cell aggregates into the body without immune rejection of the cells. Altman et al. (Diabetes 36:625–633 (1986)) have placed portions of insulinomas inside tubular membranes for implantation, and Reach et al. (Diabetes 33:752–761 (1984)) have used a U-shaped ultra-filtration design for implantation. Brauker et al. U.S. Pat. No. 5,314,471 describes a relatively small, compact implant assembly capable of inducing appropriate vascularization while providing immunoprotection for enclosed cells or cell aggregates.

SUMMARY OF THE INVENTION

The present invention provides a means for encapsulating cells and/or cellular aggregates in a very small volume of a gellable material to enable implantation of the cells and/or cellular aggregates into a patient. The capsules created are called minimum volume capsules, or MVCs, due to the small volume encapsulated. This has tremendous advantages of creating very little wasted space and being amenable to providing the immunoprotection necessary for implantation.

The invention further provides means for creating MVCs in a manner which does not damage the cells and/or cellular aggregates so that viable cells and/or cellular aggregates are made available for implantation.

BRIEF DESCRIPTION OF DRAWINGS

FIG. 3a shows insulin secretion by porcine islets in response to a glucose or glucose plus IBMX stimulus.

DESCRIPTION OF THE INVENTION

Figure 1:
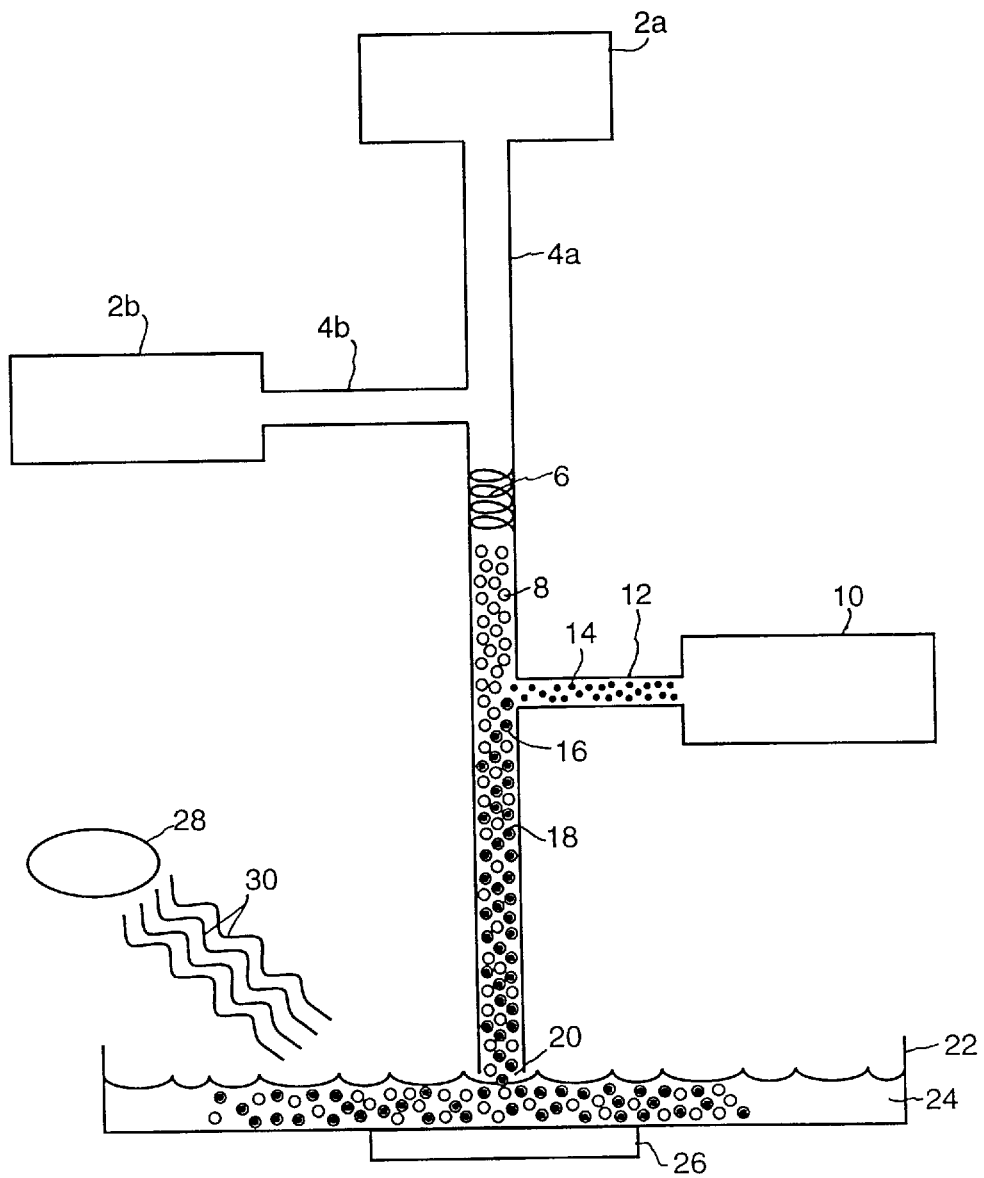
FIG. 1 shows an apparatus for continuous encapsulation of biological material.

The present invention provides methods for encapsulating biological material by engulfment of the biological material by dispersed liquid droplets of water-soluble polymeric materials in an immiscible continuous phase. The dispersed liquid droplets containing biological materials are subsequently gelled to form solid polymeric particles containing encapsulated cells and/or cellular aggregates. The volume of the dispersed liquid droplets allowed to come in contact with each piece of biological material is kept to a minimum to limit the size of the microcapsule and to avoid aggregation of microcapsules.

In a preferred embodiment, a three phase system is formed, consisting of a continuous aqueous phase, a dispersed aqueous phase, and a solid phase. The aqueous phases are composed of water soluble polymers which are mutually immiscible. The solid phase is comprised of the biological material to be encapsulated.

Batch Encapsulation

Encapsulation can be performed on a batch of biological material. In the preferred embodiment, an aqueous solution to form the dispersed phase is rapidly mixed with the continuous phase to form a uniform emulsion. The dispersed phase is itself capable of gelation or contains a component capable of gelation. The biological material is then added to the emulsion with gentle mixing.

The biological material is coated with the contents of the dispersed phase by collision of liquid droplets with the biological material. Gelation is then induced.

In an alternative embodiment, an aqueous solution of biological material is added to the continuous aqueous phase. The water solution added with the biological material is dispersed in the continuous phase, leaving solid particles of biological material suspended in the continuous phase. The second aqueous liquid phase is then dispersed into the continuous phase in the form of small droplets. As with the previous embodiment, the biological material is coated with the contents of the dispersed phase by collision of liquid droplets with the biological material, and gelation is then induced.

In a third embodiment, an aqueous solution of biological material is added to the to-be-dispersed phase before dispersion. The water from the aqueous biological material solution disperses into the to-be-dispersed phase, leaving solid particles of biological material suspended in the to-be-dispersed phase. This mixture is then dispersed into the continuous phase to form small droplets. As the droplets form, excess dispersed phase material is stripped from the droplets, leaving a sufficient amount to coat the biological material. Gelation is then induced.

Continuous Encapsulation

Alternatively, encapsulation can be a continuous procedure with all components flowing together continually to create microcapsules. Both components for the continuous and dispersed phases are fed into a chamber with continuous mixing to create the emulsion. The emulsion flows through the chamber past the feed of biological material, which joins the flow. Gentle mixing is provided, either by configuration of the tubing or by external means, and engulfment of the biological material occurs. The engulfed biological material continues to flow into a curing compartment where gelation is induced.

FIG. 1 shows a device for the continuous production of MVCs. This device is optionally sterilizable in order to maintain the sterility of the biological material and the MVCs. This can be accomplished for example by assembling the apparatus aseptically from sterilized parts, such as autoclaved components, or the apparatus can be constructed of materials that allow for the system to be sterilized using steam-in-place or other sterilizing techniques.

Peristaltic or other pumps (2a and 2b) are connected to tubing (4a and 4b) through which the continuous phase and the dispersed phase materials are pumped. In-line mixer elements (6) mix the materials and create an emulsion (8). Another peristaltic or other pump (10) attached to a feed line (12) for biological material (14) pumps the biological material into the emulsion stream. Gentle mixing is provided in the stream beyond the joint (16). Engulfment occurs in the stream. The outlet (20) provides a gentle steady stream of effluent collected into a tank (22) containing physiologically compatible solution containing the curing material (24). The curing material will vary depending on the method of gelation. Optionally a light source (28) is present to provide light (30) of the appropriate wavelength for photopolymerization. Gentle stirring as by a stirrer (26) such as a magnetic stirrer prevents aggregation of nascent capsules during curing.

Engulfment

Compounds for the continuous and dispersed phases are chosen so as to create the appropriate differential in surface tension relative to the biological material. This allows the dispersed phase to engulf the biological material, while the continuous phase does not. The thermodynamic equation governing particle engulfment is as follows: for a particle (P) suspended in a continuous phase (C) coming into contact with a disperse phase (D), the interfacial tension between each of these components can be expressed in the form $\gamma_{ij}$ where $\gamma_{pc}$, $\gamma_{pd}$, and $\gamma_{dc}$ represent the interfacial tensions between the particle and continuous phase, the particle and discontinuous phase and the continuous and discontinuous phases respectively. The thermodynamic work of engulfment ($\Delta F_{engulf}$) is the sum of the interfacial tensions formed and the interfacial tensions lost:

$$\Delta F_{engulf} = \gamma_{pd} - \gamma_{pc} - \gamma_{dc}$$

Engulfment occurs when the Helmholtz free energy of the system is negative ($\Delta F_{engulf} < 0$). See Omenyi, S. N. et al., J. Appl. Phys. 52:789–802 (1980).

Further, compounds for the two aqueous phases must be biocompatible. By "biocompatible" is meant materials which produce a minimal or no adverse response in the body at the concentrations used.

METHODS IN ENZYMOLOGY Vol. 228, esp. pp. 3–13, (1994) (eds.) Academic Press Limited, London, (incorporated herein by reference) provides an in depth description of methods for determining the usable combinations of polymers to induce partitioning of the biological material into the dispersed phase. Further, Table I lists a variety of polymer combinations which are effective in partitioning. Id. at 4.

For example, the continuous phase polymer can be selected from, but is not limited to, the following group: poly(ethylene glycol), poly(ethylene glycol propylene glycol), poly(vinyl alcohol), benzoyldextran, hydroxypropyl dextran, Ficoll, polyvinylpyrrolidone, poly(styrene sulfonate), DEAE-dextran and acrylic copolymers. The dispersed phase polymer can be selected from, but is not limited to, the following group: dextran, benzoyldextran, hydroxypropyl starch, poly(vinyl alcohol), maltodextrin, pullulan, poly(vinyl methyl ether), dextran sulfate, carboxymethyl dextran, poly(acrylic acid) and poly (acrylamide).

An example of a polymer combination which can be used for the present invention is the preferred embodiment of poly(ethylene glycol) (PEG) (Fluka Biochemika) in isotonic saline to create the continuous phase in combination with dextran (ICN Biomedical) in isotonic saline to create the dispersed phase. The PEG is dissolved in physiologic saline at a concentration of between 5 and 50% (w/w), preferably between 5 and 25% (w/w), more preferably between 5 and 15% (w/w), and most preferably at about 10% (w/w). The molecular weight of the PEG is between 1 and 100 kD, preferably between 1 and 40 kD, more preferably between 6 and 10 kD, and most preferably about 8 kD. The dextran is dissolved in physiologic saline at a concentration of between 5 and 50% (w/w), preferably between 5 and 25% (w/w), more preferably between 5 and 15% (w/w), and most preferably at about 10% (w/w). Molecular weight of the dextran is between 10 and 400 kD, preferably between 10 and 200 kD, more preferably between 100 and 200 kD, and most preferably about 150 kD.

Gelation

The discontinuous phase is either itself capable of gelation or includes a gellable component.

The gelling agent must be gellable under conditions which do not damage the biological material. Thus, gelation can occur for example by changing the conditions of temperature, pH or ionic environment, or by photopolymerization.

Ionic bonding of the compound to physiologically compatible ions such as Ca++ or Ba++ to form polymers is one acceptable mode. Examples of compounds capable of such gelation are acidic, water-soluble polysaccharides such as alginate, carrageenan, guar gum, xanthan gum, gum arabic, pectin and tragacanth gum. In the preferred embodiment, alginate (Pronova Biopolymer) is dissolved in the dispersed phase at a concentration of 0.4 to 4.0% (w/w), preferably 0.4 to 2.0% (w/w), more preferably 1.2 to 1.8% (w/w), and most preferably about 1.6% (w/w). Alginate high in guluronic acid content is preferred. Gelation is induced by the addition of divalent cations such as Ca++ or Ba++.

Other means of gelation such as photopolymerization are also acceptable. Hubbell et al. U.S. Pat. No. 5,410,016 (incorporated herein by reference) and Hubbell et al. U.S. Ser. No. 07/958,870 (now, U.S. Pat. No. 5,529,914) (incorporated herein by reference) describe a variety of compounds which can be photopolymerized to create a microcapsule. Examples of such compounds include macromers which are water soluble compounds and are non-toxic to biological material before and after polymerization, and contain at least two free radical-polymerizable regions. The macromers can optionally have a biodegradable region. Examples of macromers for photopolymerization include unsaturated derivatives of poly(ethylene oxide) (PEO), PEG, poly(vinyl alcohol) (PVA), poly(vinylpyrrolidone) (PVP), poly(ethyloxazoline) (PEOX), poly(amino acids), polysaccharides such as alginate, hyaluronic acid, chondroitin sulfate, dextran, dextran sulfate, heparin, heparin sulfate, heparan sulfate, chitosan, gellan gum, xanthan gum, guar gum, water soluble cellulose derivatives and carrageenan, and proteins such as gelatin, collagen and albumin The macromers are mixed with photosensitive chemicals or dyes to allow gelation by shining light of the appropriate wavelength on the engulfed biological material.

Further, mild heating which does not harm the biological material can be used for gelation. Example of a gellable material in this category is low-temperature melting agarose.

Biological Material

By "biological material" is meant mammalian tissue, cellular aggregates, individual cells, sub-cellular organelles and other isolated sub-cellular components. Examples of cells which can be encapsulated are primary cultures as well as established cell lines, including transformed cells. These include but are not limited to pancreatic islets of Langerhans, hepatocytes, parathyroid cells, foreskin fibroblasts, Chinese hamster ovary cells, beta cell insulomas, lymphoblastic leukemia cells, mouse 3T3 fibroblasts, dopamine secreting ventral mesencephalon cells, neuroblastoid cells, adrenal medulla cells, and T-cells. As can be seen from this partial list, cells of all types, including dermal, neural, blood, organ, muscle, glandular, reproductive, and immune system cells can be encapsulated successfully by this method. Additionally, proteins (such as hemoglobin), polysaccharides, oligonucleotides, enzymes (such as adenosine deaminase), enzyme systems, bacteria, microbes, vitamins, cofactors, blood clotting factors, drugs (such as TPA, streptokinase or heparin), antigens for immunization, hormones, and retroviruses for gene therapy can be encapsulated by these techniques.

Removal of Biological Material Partially Encapsulated

Fully encapsulated biological material does not adhere to tissue culture gel matrix. However, partially encapsulated biological material can be induced to adhere to the gel matrix through outgrowth of associated anchorage-dependent fibroblasts. Relying on this characteristic, an assay was developed to determine the percent of microcapsules which only partially encapsulated the biological material. Microcapsules can be plated on a suitable medium such as Matrigel (Collaborative Biomedical Products) and allowed to grow in culture conditions for a period of around two weeks. The Matrigel or its equivalent enables anchorage of the cells. Fully encapsulated biological material will remain in suspension, while partially encapsulated biological material will adhere to the gel matrix. The supernatant can be removed along with the suspended microcapsules as a means for purifying the fully encapsulated biological material from that only partially encapsulated.

Further Modifications

The microcapsules of this invention can be further modified to create additional layers and/or membranes such as by the addition of polycationic layers. These additional layers can provide added structural stability and/or permselectivity. For example, when the gelled material is a polyanionic polymer such as alginate, polylysine or other polyamines can be ionically bound to the outside to create a membrane. See Lim U.S. Pat. No. 4,352,883, Lim U.S. Pat. No. 4,391, 909, Lim U.S. Pat. No. 4,409,331, Tsang et al. U.S. Pat. No. 4,663,286, Goosen et al. U.S. Pat. No. 4,673,566, Goosen et al. U.S. Pat. No. 4,689,293, Rha et al. U.S. Pat. No. 4,744,933, Rha et al. U.S. Pat. No. 4,749,620, Goosen et al. U.S. Pat. No. 4,806,355, and Hubbell et al. U.S. Pat. No. 5,380,536, incorporated herein by reference, for descriptions of methods for making such a membrane.

Alternatively, additional membranes can be created around the microcapsules without relying on interactions with the gelled material. For example, the methods of Hubbell et al., U.S. Ser. No. 07/958,870 (now, U.S. Pat. No. 5,529,914) can be utilized to create an additional photopolymerized coat around the microcapsules of this invention.

Implantation

The microcapsules are preferably gently washed and collected after gelation and any additional modifications. The encapsulated biological material can be implanted in a patient to provide compositions secreted by the encapsulated material, or to provide the encapsulated material itself. For example, with encapsulation of islets of Langerhans, the microcapsules can be implanted in a diabetic animal for treatment of diabetes through the production of insulin.

EXAMPLE 1

Batch Encapsulation of Islets of Langerhans

A batch of Islets of Langerhans was prepared for encapsulation. 100 to 50,000 islets, preferably between 5,000 and 30,000 islets, and most preferably between 15,000 and 25,000 islets were used. Islets were maintained in culture for from 0 to 72 hours, preferably between 6 and 24 hours, and most preferably overnight after isolation. Islets were pooled to a single 50 ml centrifuge tube. The islets were centrifuged to form a pellet (40 g for 4 minutes). The culture supernatant was removed and the islet pellet resuspended in isotonic saline containing 10 mM HEPES. The washing procedure was preferably repeated three times to remove excess proteins from the islets.

A sample of washed resuspended islets was removed for counting to determine the correct volume to use for the procedure. The appropriate number of washed islets were then pelleted and the supernatant replaced with a 5:1 volume ratio of 10% dextran and 1.6% alginate mixture. The islets were gently mixed in this solution. Alternatively, the pelleted islets were directly resuspended in about 1 ml isotonic saline.

A uniform emulsion containing a 20:5:1 volume ratio of 10% PEG:10% dextran:1.6% alginate was prepared in a separate 50 ml centrifuge tube by vigorous mixing using a vortex mixer or equivalent. The islets in the dextran-alginate mixture were pelleted and the supernatant removed to leave a concentrated islet suspension in about 1 ml of solution.

The freshly prepared uniform emulsion was quickly added to the islet suspension, and the tube was gently mixed using a rocking table or by hand to prevent distinct phase separation of the dextran and PEG phases. This mixing lasted for between 1 and 15 minutes, preferably between 5 and 15 minutes, and most preferably between 8 and 12 minutes.

The emulsion containing islets was then slowly poured into a 250 ml beaker containing 150 ml of gently stirred curing buffer containing 10 mM HEPES isotonic saline supplemented with barium or calcium chloride between 10 and 100 mM, preferably between 10 and 50 mM, and most preferably between 10 and 30 mM divalent metal salts. The stirring was used to prevent aggregation of the nascent capsules during ionic cross-linking and to ensure dissolution of the water-soluble dextran and PEG away from the capsules.

The nascent capsules were then allowed to settle and cure in the curing buffer for between 2 and 30 minutes, preferably between 2 and 20 minutes, most preferably between 5 and 15 minutes. The supernatant above the settled capsules was slowly decanted and the capsules were rinsed with fresh curing buffer. By repeating the process of resuspension and decanting, empty capsules can be removed from the preparation.

The resuspended capsules were transferred to a fresh 50 ml centrifuge tube and centrifuged at 40 g for 4 minutes in the cold (2° C. to 8° C.). The supernatant was removed and the capsules resuspended and washed in buffered isotonic saline. The fully cured encapsulated islets were resuspended and washed three times in culture media. The encapsulated islets were resuspended in culture media and maintained in culture using standard methods for islet culture.

EXAMPLE 2

Continuous Encapsulation of Islets of Langerhans

A batch of Islets of Langerhans is prepared for encapsulation. 100 to 50,000 islets, preferably between 5,000 and 30,000 islets, and most preferably between 15,000 and 25,000 islets are used. Islets are maintained in culture for from 0 to 72 hours, preferably between 6 and 24 hours, and most preferably overnight after isolation. Islets are pooled to a single 50 ml centrifuge tube. The islets are centrifuged to form a pellet (40 g for 4 minutes). The culture supernatant is removed and the islet pellet resuspended in isotonic saline containing 10 mM HEPES. The washing procedure is preferably repeated three times to remove excess proteins from the islets.

The islets are resuspended to a concentration of between 1,000 to 40,000 islets/ml, preferably between 5,000 and 30,000 islets/ml, and most preferably to between 18,000 and 22,000 islets/ml in an isotonic saline solution.

The apparatus for continuous encapsulation of islets is prepared as follows. Peristaltic pumps are attached to tubing such that a controlled feed of PEG at a rate of about 20 ml/min is maintained through one tube and a controlled feed of dextran or a solution containing dextran and alginate at a volume ratio of 5:1 at a rate of about 5 ml/min is maintained through the other tube. The tubes are arranged so that they join together into one channel with the PEG and dextran or dextran/alginate flows concomitantly joining together. In-line mixing elements then act on the mixture in the channel to create an emulsion wherein the PEG is in the continuous phase and the alginate and/or dextran are in the dispersed phase. An additional tube joins the channel, and islets suspended in either saline or alginate are pumped through this third tube at a rate of about 1 ml/min. The islet feed stream is gently mixed with the emulsified carrier stream through the configuration of the islet feed stream inlet into the channel; The channel outlet, provides a gentle steady stream of effluent collected into a gently stirred tank containing curing buffer composed of 10 mM HEPES isotonic saline supplemented with barium or calcium chloride between 10 and 100 mM, preferably between 10 and 50 mM, and most preferably between 10 and 30 mM divalent metal salts. The stirring was used to prevent aggregation of the nascent capsules during ionic cross-linking and to ensure dissolution of the water-soluble dextran and PEG away from the capsules.

The nascent capsules are then allowed to settle and cure in the curing buffer for between 2 and 30 minutes, preferably between 2 and 20 minutes, most preferably between 5 and 15 minutes. The supernatant above the settled capsules is slowly decanted and the capsules are rinsed with fresh curing buffer. By repeating the process of resuspension and decanting, empty capsules can be removed from the preparation.

The resuspended capsules are transferred to a fresh 50 ml centrifuge tube and centrifuged at 40 g for 4 minutes in the cold (2° C. to 8° C.). The supernatant is removed and the capsules resuspended and washed in buffered isotonic saline. The fully cured encapsulated islets are resuspended and washed three times in culture media. The encapsulated islets are resuspended in culture media and maintained in culture using standard methods for islet culture.

EXAMPLE 3

Separation of Fully Encapsulated Islets of Langerhans

To estimate the number of partially encapsulated islets, a fibroblast outgrowth assay was developed. Anchorage-dependent fibroblasts are routinely found associated with islets even after several days of culture. Encapsulated islets were plated onto Matrigel gel matrix which provides support for the rapid growth of anchorage dependent cells such as fibroblasts. Full encapsulation of an islet would prevent fibroblast outgrowth from the islet to the growth matrix, hence fibroblast only occurs from partially encapsulated islets.

Figure 2:
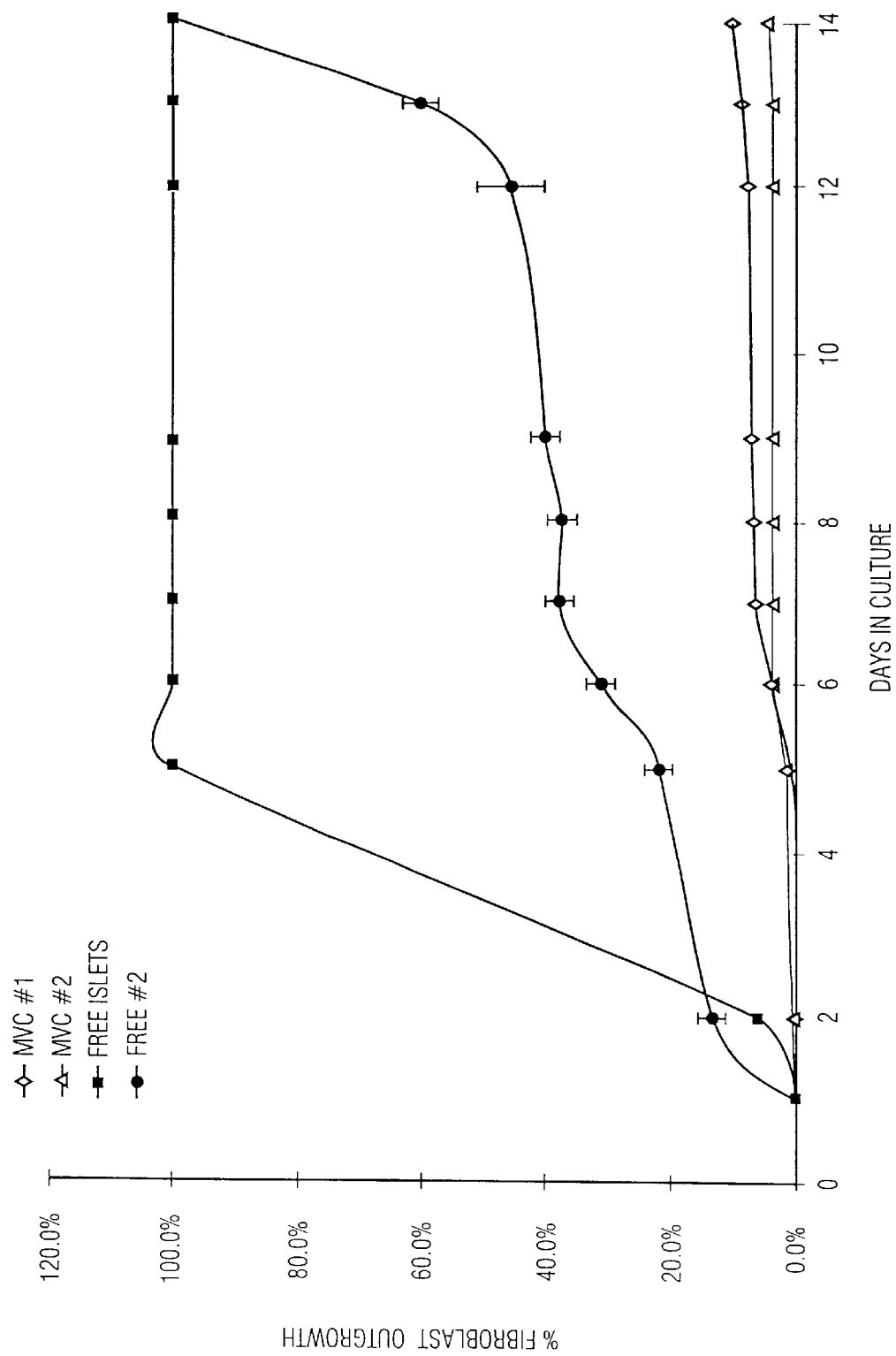
FIG. 2 shows fibroblast outgrowth from free and encapsulated islets of Langerhans.

Two batches of free or encapsulated islets were tested. Approximately 100 islets or encapsulated islets were counted out into tissue culture treated wells coated with Matrigel. The number of islets from which fibroblast outgrowth occurred was measured over a 2 week study period. FIG. 2 shows the percent fibroblast outgrowth of two encapsulated cultures and two unencapsulated control cultures over time. Approximately 10% of the encapsulated islets demonstrated fibroblast outgrowth, indicating approximately 90% of the islets were completely encapsulated by the method.

The fully encapsulated islets were then segregated from the partially encapsulated islets. This was accomplished by culturing the encapsulated islets on Matrigel coated tissue culture plates for between 3 and 7 days. Partially encapsulated islets demonstrated fibroblast outgrowth and were irreversibly adhered to the Matrigel by the fibroblasts. Fully encapsulated islets remained in suspension and were removed by removal of the growth medium. The capsules were then washed prior to either further culturing or implantation.

EXAMPLE 4

In Vitro Characterization of Encapsulated Islets

Figure 3B:
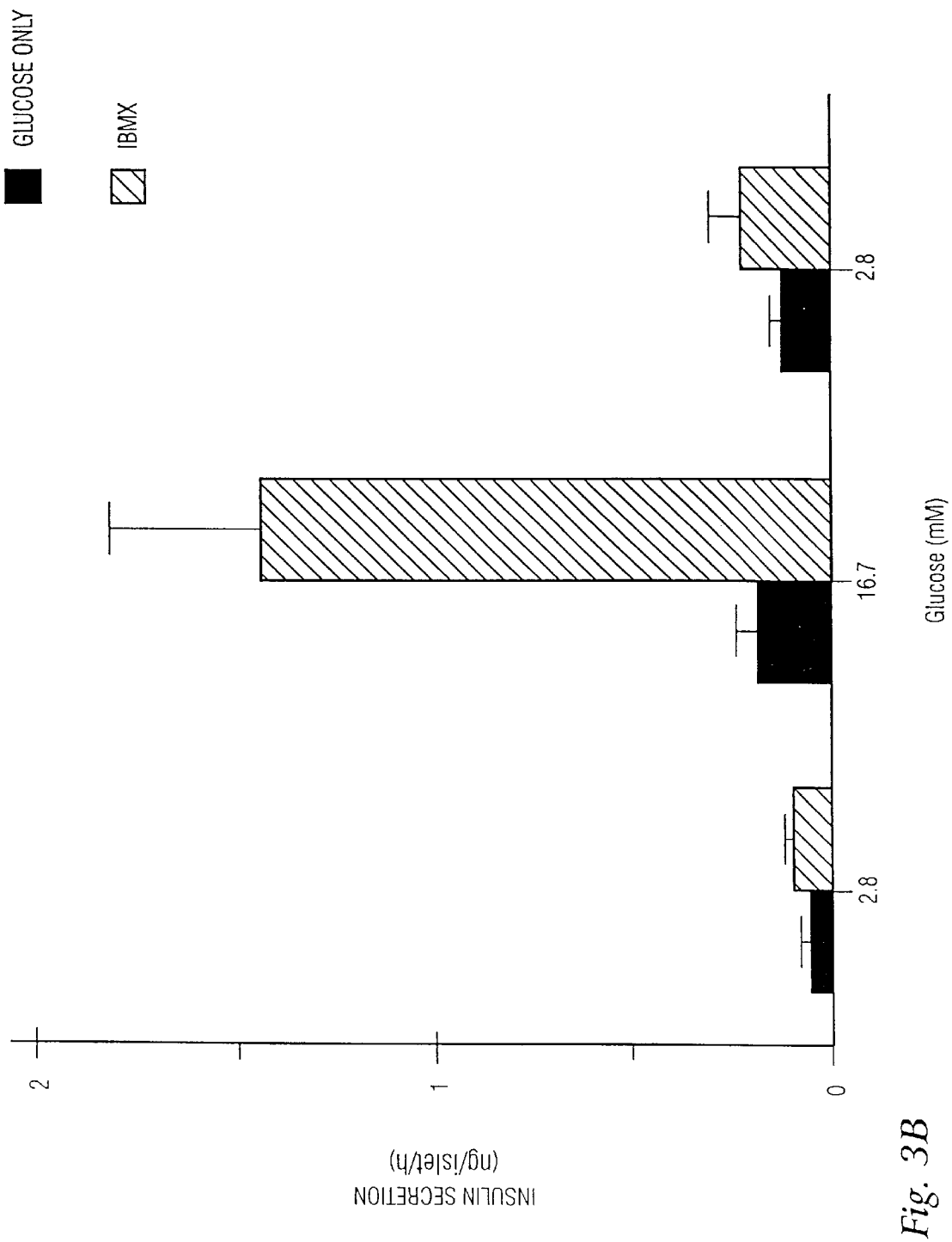
FIG. 3b shows the same for MVC encapsulated porcine islets.

The ability of encapsulated porcine islets of Langerhans to respond to a change in glucose concentration was measured using a static glucose stimulation assay performed either in the presence or absence of isobutyl methyl xanthine (IBMX), a potentiator of insulin secretion in response to a glucose challenge. These results were compared to those obtained for free pig islets. The results of these assays are summarized in FIG. 3a and 3b. FIG. 3a shows the response of unencapsulated islets, while FIG. 3b shows the response of capsules encapsulated according to the invention. This figure demonstrates that the encapsulated islets are responsive to glucose concentration and secrete insulin in the same manner as unencapsulated islets.

EXAMPLE 5

In Vivo Performance of Encapsulated Islets

The ability of encapsulated porcine islets to function in vivo was assayed using diabetes correction studies with STZ-diabetic athymic mice. See Juno, A. et al., J. Clin. Invest. 48:2129–2139 (1969) for a description of STZ induced diabetes. The number of islet equivalents implanted into the kidney capsule of STZ-athymic mice, either as free or encapsulated islets, required to achieve correction was measured.

Figure 4:
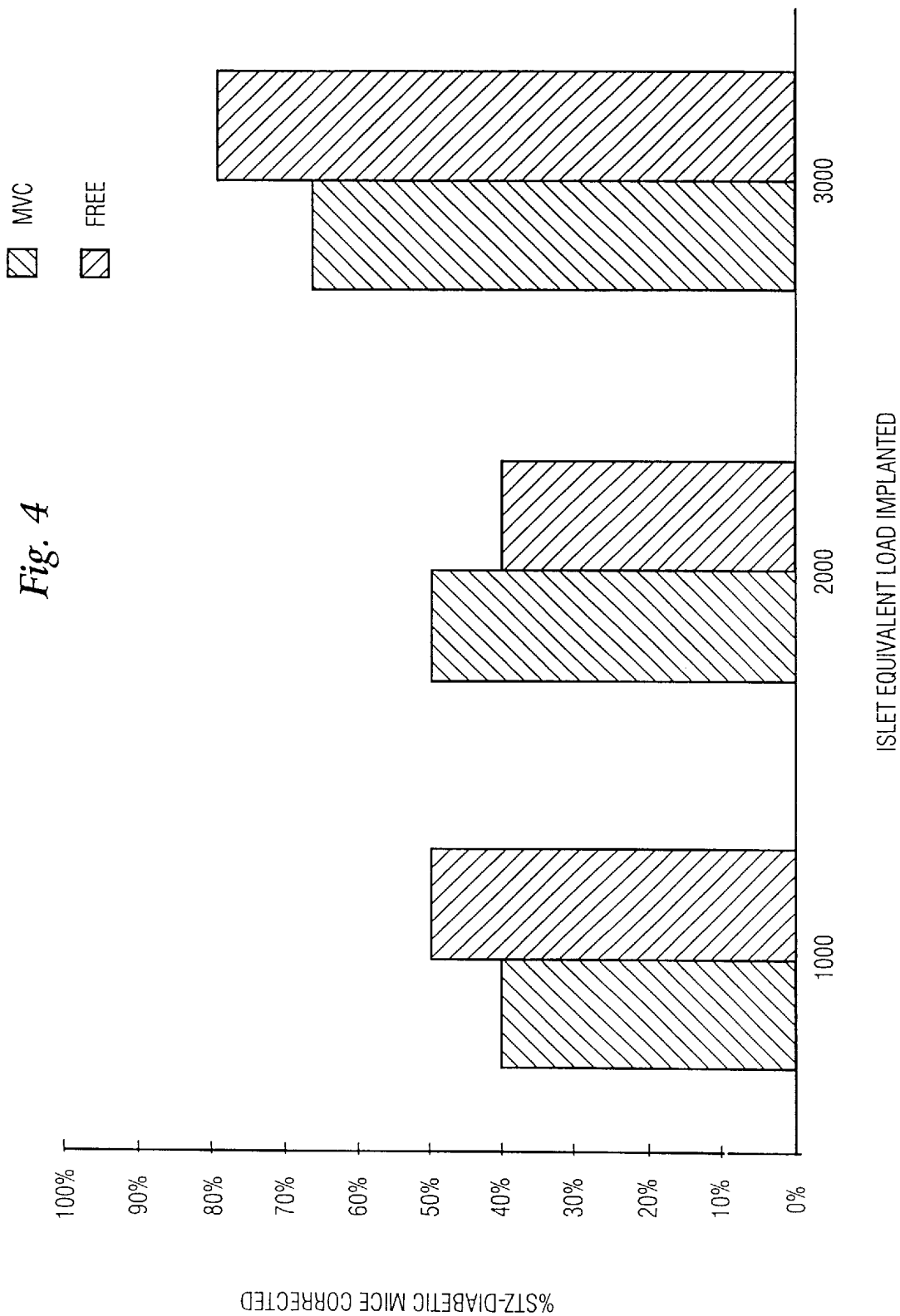
FIG. 4 shows STZ-diabetes correction in athymic mice using MVC encapsulated porcine islets.

The results of these assays are presented in FIG. 4. As can be seen from the data, islets encapsulated according to the present invention are equally effective as unencapsulated islets in correcting STZ-diabetes.

Figure 5:
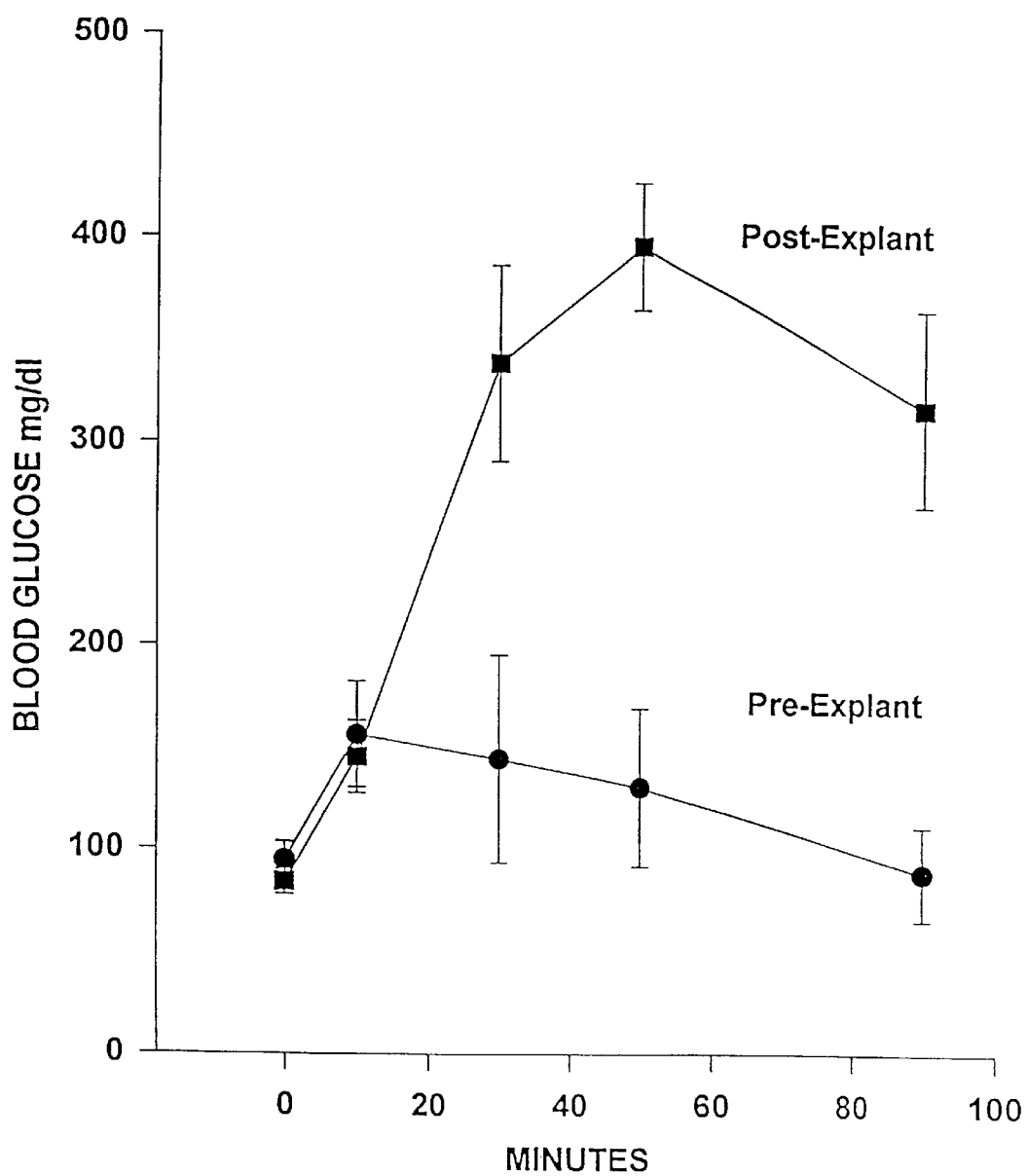
FIG. 5 shows a glucose-tolerance test on an athymic mouse implanted with rat islets in MVCs, both before and after removal of the implanted MVCs.

The in vivo effectiveness of islets encapsulated in MVCs was further analyzed using glucose tolerance testing (GTT) in athymic mice. FIG. 5 shows the results of GTT in mice six months after implantation of rat islets in MVCs both prior to (●) and after (■) explantation of the MVCs. As can be seen from the figure, the implanted MVCs were capable of maintaining glucose at appropriate levels, while after explantation of the MVCs, the blood glucose returned to diabetic levels.

The Examples included herein are not to be construed as limiting on the invention, but are provided to illustration some variations of the invention. The invention is to be limited only by the claims that follow.

I claim:

1. A method for encapsulating biological material in minimal volume capsules comprising
    a. preparing an emulsion comprising a continuous phase biocompatible aqueous polymeric solution, a dispersed phase biocompatible aqueous polymeric solution and said biological material wherein the surface tension of the continuous phase, the dispersed phase and the biological material are thermodynamically related so as to induce engulfment of the biological material by the dispersed phase, and wherein the dispersed phase comprises a gellable component;
    b. allowing the dispersed phase of the emulsion to engulf the biological material; and
    c. gelling the gellable component of the dispersed phase.

2. The method of claim 1 wherein the continuous phase is an aqueous solution comprising a polymer selected from the group consisting of poly(ethylene glycol), poly(ethylene glycol propylene glycol), poly(vinyl alcohol), benzoyldextran, hydroxypropyl dextran, nonionic synthetic polymer of sucrose and polyvinylpyrrolidone.

3. The method of claim 1 wherein the dispersed phase is an aqueous solution comprising a polymer selected from the group consisting of dextran, benzoyldextran, hydroxypropyl starch, poly(vinyl alcohol), maltodextrin, pullulan, poly(vinyl methyl ether), dextran sulfate, carboxymethyl dextran, poly(acrylic acid) and poly(acrylamide).

4. The method of claim 1 wherein the biological material is selected from the group consisting of mammalian cells, cell aggregates and tissue.

5. The method of claim 4 wherein the biological material is selected from the group consisting of pancreatic islets of Langerhans, hepatocytes, parathyroid cells, foreskin fibroblasts, Chinese hamster ovary cells, beta cell insulomas, lymphoblastic leukemia cells, mouse 3T3 fibroblasts, dopamine secreting ventral mesencephalon cells, neuroblastoid cells, adrenal medulla cells, and T-cells.

6. The method of claim 5 wherein the biological material is pancreatic islets of Langerhans.

7. The method of claim 1 wherein the biological material is selected from the group consisting of sub-cellular organelles and other sub-cellular components.

8. The method of claim 6 wherein the biological material is selected from the group consisting of proteins, polysaccharides, oligonucleotides, enzymes, enzyme systems, bacteria, microbes, vitamins, cofactors, blood clotting factors, drugs, antigens, hormones, and retroviruses.

9. The method of claim 1 wherein the biological material is added to the continuous phase prior to emulsion formation.

10. The method of claim 1 wherein the biological material is added to the dispersed phase prior to emulsion formation.

11. The method of claim 1 wherein the biological material is added after emulsion formation.

12. A method for encapsulation of islets of Langerhans in minimal volume capsules comprising
    a. preparing an emulsion comprising a continuous. phase biocompatible aqueous solution comprising poly(ethylene glycol), a dispersed phase biocompatible aqueous polymeric solution comprising dextran and alginate, and said islets wherein the surface tension of the continuous phase, the dispersed phase and the biological material are thermodynamically related so as to induce engulfment of the biological material by the dispersed phase;
    b. allowing the dispersed phase of the emulsion to engulf the islets; and
    c. gelling the alginate.

13. The method of claim 12 wherein the islets are added to the emulsion of the continuous phase and the dispersed phase.

14. The method of claim 12 wherein the islets are added to the continuous phase before the emulsion is formed.

15. The method of claim 12 wherein the islets are added to the dispersed phase before the emulsion is formed.

* * * * *

UNITED STATES PATENT AND TRADEMARK OFFICE
CERTIFICATE OF CORRECTION

PATENT NO. : 5,827,707
DATED : October 27, 1998
INVENTOR(S) : Francis Lamberti

It is certified that error appears in the above-identified patent and that said Letters Patent is hereby corrected as shown below:

Column 7, line 53, change "outlet," to --outlet--.

Signed and Sealed this

Twenty-second Day of June, 1999

Attest:

Q. TODD DICKINSON

*Attesting Officer*     *Acting Commissioner of Patents and Trademarks*